US009062623B2

(12) United States Patent
Verdier et al.

(10) Patent No.: US 9,062,623 B2
(45) Date of Patent: Jun. 23, 2015

(54) METHOD AND DIAGNOSTIC DEVICE FOR DIAGNOSING A HEATABLE EXHAUST GAS SENSOR OF AN INTERNAL COMBUSTION ENGINE

(75) Inventors: Cyril Verdier, Stuttgart (DE); Stefan Klein, Deizisau (DE); Gerhard Lemke, Esslingen (DE); Karsten Glashoff, Deizisau (DE); Peter Brida, Filderstadt (DE); Frank Meier, Kornwestheim (DE); Thomas Seiler, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 743 days.

(21) Appl. No.: 13/381,437

(22) PCT Filed: Jun. 30, 2010

(86) PCT No.: PCT/EP2010/059251
§ 371 (c)(1),
(2), (4) Date: Mar. 23, 2012

(87) PCT Pub. No.: WO2011/000853
PCT Pub. Date: Jan. 6, 2011

(65) Prior Publication Data
US 2012/0167656 A1    Jul. 5, 2012

(30) Foreign Application Priority Data
Jul. 1, 2009  (DE) .......................... 10 2009 027 378

(51) Int. Cl.
*G01N 37/00*    (2006.01)
*F02D 41/14*    (2006.01)
(Continued)

(52) U.S. Cl.
CPC ........ *F02D 41/1495* (2013.01); *F02D 41/1494* (2013.01); *F02D 41/266* (2013.01); *G01N 27/4175* (2013.01)

(58) Field of Classification Search
None
See application file for complete search history.

(56) References Cited

U.S. PATENT DOCUMENTS

| 4,532,013 | A  | 7/1985 | Dietz et al. |
| 5,781,878 | A  | 7/1998 | Mizoguchi et al. |
| 6,266,993 | B1 | 7/2001 | Diehl et al. |

(Continued)

FOREIGN PATENT DOCUMENTS

| CN | 1493774   | 5/2004  |
| CN | 1576837   | 2/2005  |
| DE | 31 15 404 | 11/1982 |
| DE | 196 22 625| 12/1996 |

(Continued)

*Primary Examiner* — Robert R Raevis
(74) *Attorney, Agent, or Firm* — Kenyon & Kenyon LLP (57) ABSTRACT

A method is described for diagnosing a heatable exhaust gas sensor of an internal combustion engine, in which a predefined chronologically varying or constant voltage or a predefined chronologically varying or constant current is generated with the aid of a voltage source, the voltage or the current is applied to terminals of the exhaust gas sensor, a current or applied voltage, which flows through the voltage source when the voltage or the current is applied, is detected, and the current or the voltage is analyzed to diagnose the exhaust gas sensor. To diagnose the exhaust gas sensor, which permits a reliable and accurate diagnosis of the exhaust gas sensor and allows a statement about the type of a possibly existing error on the exhaust gas sensor, the method is executed independently of a control and/or regulating unit of the internal combustion engine, an operating temperature of the exhaust gas sensor being regulated to a predefined temperature value with the aid of a regulating element, which is separate from the control and/or regulating unit.

26 Claims, 7 Drawing Sheets

(51) Int. Cl.
*G01N 27/417* (2006.01)
*F02D 41/26* (2006.01)

(56) References Cited

U.S. PATENT DOCUMENTS

2004/0221641 A1  11/2004  Moritsugu et al.
2006/0137427 A1*  6/2006  Schnaibel et al. ............ 73/1.06
2009/0095048 A1*  4/2009  Sakai et al. .................. 73/1.06

FOREIGN PATENT DOCUMENTS

| | | |
|---|---|---|
| DE | 197 16 173 | 10/1998 |
| DE | 198 45 927 | 4/2000 |
| DE | 10 2006 014 266 | 6/2007 |
| EP | 1 480 039 | 11/2004 |
| JP | 59065249 * | 4/1984 |
| JP | 11-153569 | 6/1999 |
| JP | 2000-111514 | 4/2000 |

* cited by examiner

METHOD AND DIAGNOSTIC DEVICE FOR DIAGNOSING A HEATABLE EXHAUST GAS SENSOR OF AN INTERNAL COMBUSTION ENGINE

FIELD OF THE INVENTION

The present invention relates to a method for diagnosing a heatable exhaust gas sensor of an internal combustion engine and a diagnostic device.

BACKGROUND INFORMATION

Equipping internal combustion engines, in particular internal combustion engines for motor vehicles, with one or more exhaust gas sensors is generally known. The exhaust gas sensors are typically connected to a control and/or regulating unit of the internal combustion engine, so that the control and/or regulating unit may detect information about the composition of exhaust gases exiting from combustion chambers of the internal combustion engine. Typically at least one lambda sensor, which may be used to detect an oxygen concentration in the exhaust gas, is provided as an exhaust gas sensor in an internal combustion engine. This allows a conclusion to be drawn about an air/fuel ratio in the combustion chamber, so that the internal combustion engine may be regulated in such a way, for example, that emission regulations are met.

The lambda sensors may be divided into so-called bistable sensors and broadband sensors. The broadband sensors may in turn be designed to be single-cell broadband sensors or to be dual-cell broadband sensors. A bistable sensor has a rather high sensitivity for an excess-air ratio of the exhaust gas which is in the range of $\lambda=1$. For excess-air ratios which are not in the range of approximately $\lambda=1$, the sensitivity of the bistable sensors is relatively low. Therefore, in the case of a continually rising excess-air ratio in the exhaust gas, a jump of an output signal generated by a bistable sensor results as soon as the excess-air ratio enters the range of approximately $\lambda=1$. In contrast, broadband lambda sensors have a relatively high sensitivity also outside the range of the excess-air ratio around the value $\lambda=1$.

Modern internal combustion engines typically have one or two lambda sensors, bistable and/or broadband sensors being used for gasoline engines. Diesel engines predominantly have broadband lambda sensors.

During operation of the internal combustion engine, the control and/or regulating unit detects sensor signals which are generated by the lambda sensor or the lambda sensors and additional sensors of the internal combustion engine and operates the internal combustion engine as a function of these sensor signals. In order to be able to recognize errors in the sensors, the control and/or regulating unit checks the individual sensor signals during the operation of the internal combustion engine. In this case, the signals are typically checked as to whether electrical errors (e.g., short-circuits or line interruptions) exist. For this purpose, for example, it may be checked whether the sensor signals are in permissible value ranges. In addition, the control and/or regulating unit typically checks whether there are system errors. A system error is recognized, for example, if the variables detected with the aid of different sensors contradict one another. If the control and/or regulating unit recognizes an electrical error and/or a system error, it registers the occurrence of the error in an error memory.

Known diagnostic methods, which are performed, for example, to prepare for repairs or during maintenance work on the internal combustion engine or on a motor vehicle in which the internal combustion engine is installed, resort to the information stored in the error memory, for example. In this way, conclusions about the functionality of a lambda sensor may be drawn to a certain extent. Since there are complex interactions between various components of the internal combustion engine during operation of the internal combustion engine, however, a sufficiently secure and reliable diagnosis of an individual lambda sensor is not possible. For example, if an electrical error is recognized, it typically cannot be reliably established whether the error is based on a defect of the lambda sensor or whether the control and/or regulating unit, in particular an analysis circuit for the sensor signals of the lambda sensor, is defective. In addition, in many cases system errors may not be definitely assigned to a specific sensor, for example, a specific lambda sensor. The risk exists that the lambda sensor will be incorrectly recognized as defective, although in actuality another component of the internal combustion engine is not functioning correctly, in particular another sensor of the internal combustion engine. If a defect occurs in the internal combustion engine, cumbersome error searches may therefore occur if known diagnostic methods are used, until the actually defective component is finally identified. Reliable conclusions about the type of the error of the lambda sensor are practically impossible to be drawn in the case of known diagnostic methods.

Single-cell and dual-cell broadband lambda sensors are discussed, for example, in DE 10 2006 014 266 A1. Furthermore, detecting a leakage current between an electrode of the lambda sensor and a heating element of the lambda sensor is discussed in DE 197 16 173 A1.

SUMMARY OF THE INVENTION

The exemplary embodiments and/or exemplary methods of the present invention are based on the object of providing a method for diagnosing an exhaust gas sensor of an internal combustion engine, which permits reliable and accurate diagnosis of the exhaust gas sensor and allows a statement about the type of a possibly existing error in the exhaust gas sensor. With respect to its device aspects, the object is to provide a diagnostic device which is configured for performing the method.

These objects are each achieved by the features of the independent claims. The exhaust gas sensor may be a lambda sensor, in particular a bistable sensor, a single-cell broadband sensor, or a dual-cell broadband sensor. In the case of the diagnosis of the exhaust gas sensor with the aid of the method according to the present invention, various parameters of the exhaust gas sensor may be checked largely independently of other components of the internal combustion engine. In particular, interactions with other sensors of the internal combustion engine are prevented. Access to an error memory of the control and/or regulating unit is not necessary. The exhaust gas sensor is brought to a defined operating point by the regulation of the temperature of the exhaust gas sensor, in particular the temperature of a sensor element of the exhaust gas sensor, so that the diagnosis delivers results having a high validity and reproducibility.

The method may be executed when the internal combustion engine is shut down and is not in operation. In this case, the exhaust gas sensor may remain installed in the internal combustion engine. However, the diagnosis as per the method according to the exemplary embodiments and/or exemplary methods of the present invention may also be performed on an exhaust gas sensor which has been removed from the internal combustion engine.

Overall, a rapid and reliable check of the exhaust gas sensor for errors is made possible by the method according to the present invention. In addition, a relatively detailed appraisal of the exhaust gas sensor may be performed, which may be carried out not only within the scope of repair or maintenance work, but rather also at the end of a manufacturing process of the exhaust gas sensor, the internal combustion engine, or a motor vehicle in which the internal combustion engine is installed. It is also conceivable that the method is performed when it has been shown that a motor vehicle which was just manufactured is not functioning correctly, so that the type of the error may be analyzed more precisely with the aid of the method according to the present invention. Such a more precise analysis is also referred to as a "zero kilometer appraisal." Furthermore, lambda sensors of motor vehicles which the customer has complained about while claiming a manufacturer's warranty may be checked with the aid of the method according to the present invention.

The voltage may be applied to the terminals which are connected to electrodes of a cell, in particular a pump cell (in the case of a dual-cell sensor) or a combined pump and measuring cell (in the case of a single-cell sensor) of the exhaust gas sensor, so that a pump current which flows through the cell in the case of an intact exhaust gas sensor is detected as the current. By analyzing the detected pump current, it may be checked whether the exhaust gas sensor is functional or whether the exhaust gas sensor has an error.

The voltage may be varied step-by-step in alternating directions in such a way that the voltage successively has various voltage values, and associated current values of the current are detected for at least two of these voltage values. The two voltage values, for which the associated current values are detected, may be equal.

It may be in this case that a hysteresis with respect to the dependence between the applied voltage and the detected current is checked by analyzing the current values, which may be by comparing the current values with one another. If precisely two current values are detected for two equal voltage values, which are applied at different points in time, a difference between the two current values may be used as a measure for the hysteresis. If the absolute value of the difference is greater than a predefined threshold value, a defect, in particular blackening, i.e., ceramic reduction as a result of overloads/excessive voltages, on one of the electrodes of the cell may be inferred.

Furthermore, the voltage may be applied to the terminals which are connected to a trim resistor of the exhaust gas sensor. In this way, on the one hand, it may be checked whether the trim resistor is correctly connected within the exhaust gas sensor to the terminals of the exhaust gas sensor to which the voltage is applied or via a connection cable of the exhaust gas sensor. If the current is outside a permissible range, a poor contact of the trim resistor or an interruption of the connection between one of the terminals and the trim resistor or a shunt parallel to the trim resistor is inferred. In general, a shunt is understood as an undesirable electrically conductive path which runs parallel to a desired electrically conductive main path. If the current is within the permissible range, the value of the trim resistor may be ascertained on the basis of the current.

In this case, as a function of a value of the trim resistor that a setpoint value for the pump current in air, for example, may be ascertained, a positive pump voltage may be applied as the voltage, and the exhaust gas sensor may be checked as a function of the setpoint value and the pump current. A quotient between the pump current and the setpoint value may be ascertained in this case. If the absolute value of the quotient is greater than a predefined setpoint value, for example, a crack in a diffusion barrier or in the sensor ceramic of the cell or an electrical shunt between the electrodes of the cell is recognized. If the absolute value of the quotient is less than a further setpoint value, contaminants of the diffusion barrier ("sooting") may be recognized.

As a further check, it may be provided that a negative pump voltage is applied as the voltage, an inverted pump current is detected as the current, and it is checked whether the current is in a predefined permissible range. An excessively small current indicates a contamination of a protective layer of the exhaust gas sensor or insufficient heating of the exhaust gas sensor. If the current is excessively large, it is possible there is an electrical shunt between the electrodes or damage to or a lack of the protective layer of the sensor.

In order to recognize a shunt due to contamination, specifically sooting in an area between a sensor element and a housing of the exhaust gas sensor, the voltage may be applied between an electrode of the cell, which may be an inner electrode of a pump cell, and an electrically conductive housing part of the exhaust gas sensor, a housing current may be detected as the current, and it may be checked whether the housing current is less than or equal to a predefined maximum value. If the current exceeds the maximum value, the method establishes that soot or other, in particular metallic, deposits have accumulated between the sensor element and the housing, in particular a protective tube of the housing.

The above-described checks of the exhaust gas sensor often include a comparison of the detected current or a variable, which is formed as a function of the detected current, with predefined threshold values or predefined permissible ranges. Since different types of exhaust gas sensors are used, the threshold values or the permissible ranges must be predefined as a function of the type of the exhaust gas sensor. Furthermore, the regulation of the operating temperature must often be adapted to the type of the exhaust gas sensor. For this purpose, the type of the exhaust gas sensor may be ascertained as a function of manual inputs by a user. However, at least one measured variable which characterizes a cell resistance of the at least one cell of the exhaust gas sensor, which may be the cell resistance of a measuring cell of the exhaust gas sensor, may be detected or ascertained and a type of the exhaust gas sensor may be ascertained as a function of the measured variable. It was recognized that the individual types of the exhaust gas sensor differ in particular in their cell resistance, so that an assignment of the type to the cell resistance is possible. Operating errors by the user are largely prevented by the automatic ascertainment of the type of the exhaust gas sensor.

To ascertain the cell resistance, it may be provided that at least one measuring voltage is applied to the cell as the voltage and the current through the cell is detected as the measured variable for each measured voltage. In this way, the type of the exhaust gas sensor may be ascertained more reliably, since the resistance is not only ascertained for one voltage, but rather for multiple voltages.

In this case that at least two measuring voltages of different polarity may be applied to the cell in chronological succession. For example, in this way a statement about the ohmic resistance of the cell ceramic may be derived in the first case and a statement about the diffusion resistance of the oxygen transport to the electrode may be derived in the second case. In this way, age-related changes of the exhaust gas sensor of the same type may be differentiated from differences between exhaust gas sensors of various types. In this way, errors in the automatic recognition of the type of the exhaust gas sensor due to aging or wear of the exhaust gas sensor are at least largely prevented.

In a specific embodiment of the present invention, the or each measured variable is compared with a threshold value and the type of the exhaust gas sensor is ascertained as a function of this comparison. This means that a result of the comparison is ascertained for each measured variable and the comparison results are logically linked to one another to ascertain the type of the exhaust gas sensor.

The oxygen content of the gas to which the exhaust gas sensor is subjected forms a further influencing factor on the cell resistance. An exhaust pipe of a typical internal combustion engine, in which the exhaust gas sensor is installed, is typically sealed well in relation to the ambient air in such a way that after the shutdown of the internal combustion engine, oxygen-poor exhaust gas remains in the exhaust pipe and a gas exchange with the surroundings occurs relatively slowly. Therefore, the exhaust gas sensor may be subject to an oxygen-poor gas (excess-air ratio $\lambda<0$) during execution of the method. In order to eliminate an interfering influence as extensively as possible during the recognition of the type of the exhaust gas sensor, prior to the application of the at least one measuring voltage to the cell, a cell voltage generated by the exhaust gas on the cell may be detected and at least one measuring voltage is predefined as a function of the cell voltage. It may be provided in this case that the at least one measuring voltage is increased by the detected cell voltage.

A diagnostic device having the features of Claim 14 is proposed as a further approach to the above-mentioned object. With the aid of such a diagnostic device, the exhaust gas sensor may be checked particularly simply. For this purpose, when the engine is shut down, an electrical connection between the exhaust gas sensor and the control and/or regulating unit of the internal combustion engine is disconnected and the terminals of the exhaust gas sensor are connected to the diagnostic device. In this way, an isolated diagnosis of the exhaust gas sensor is made possible. An error on the exhaust gas sensor may either be definitively established or reliably precluded in this way.

The diagnostic device may be configured to execute the method according to the present invention and may therefore implement all advantages of the method according to the present invention. In particular, the diagnostic device may have a programmable computer, which is programmed to execute the method according to the present invention.

Further features and advantages of the exemplary embodiments and/or exemplary methods of the present invention arise from the following description, in which exemplary specific embodiments of the present invention are explained in greater detail on the basis of the drawings.

DETAILED DESCRIPTION

Figure 1:
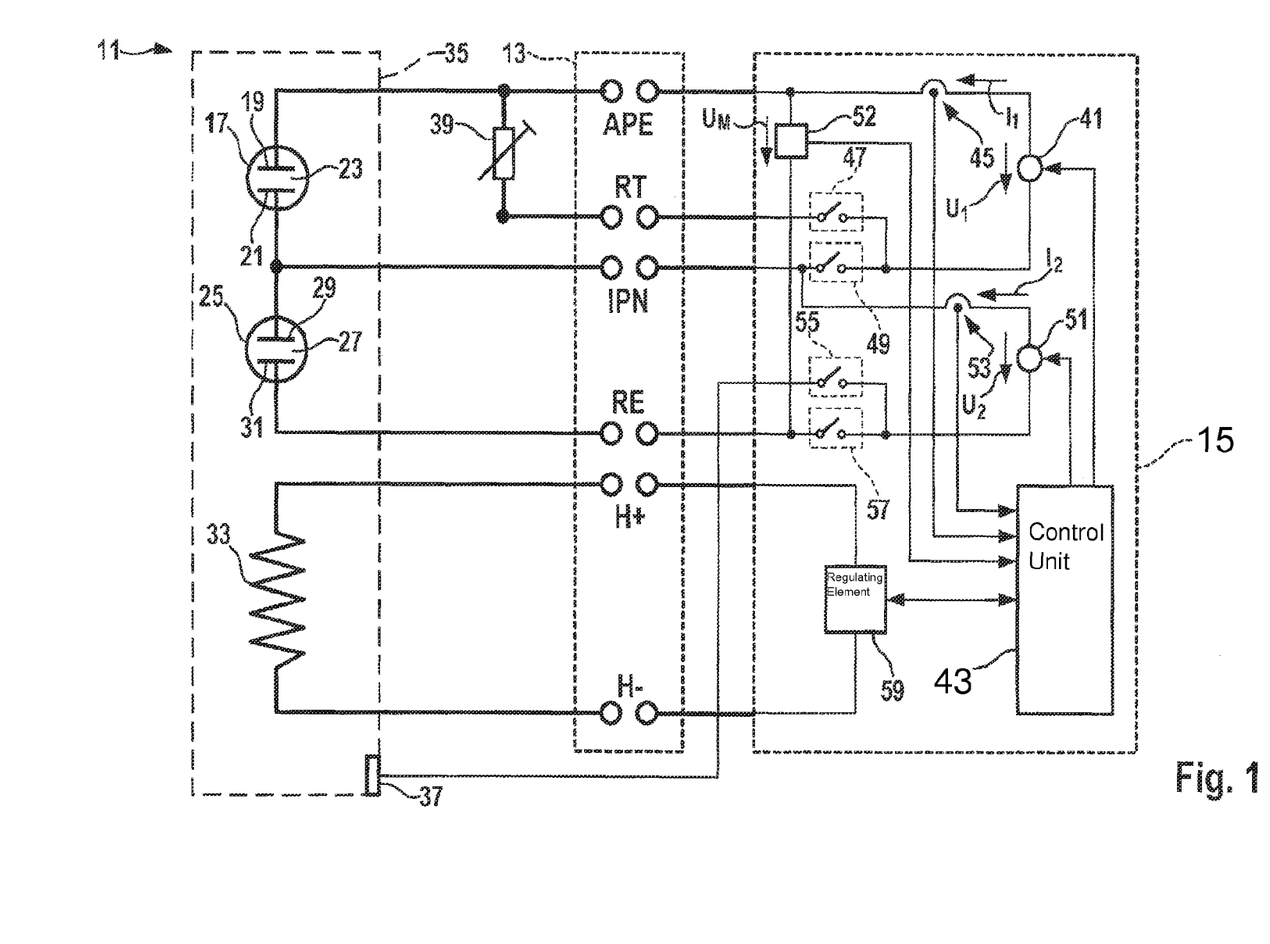
FIG. 1 shows a diagnostic device, which is connected to a dual-chamber broadband lambda sensor, in a schematic view.

The schematic view of FIG. 1 shows a dual-cell broadband lambda sensor 11, which is connected to a diagnostic device 15 via an electrical connection in the form of a plug connector 13. Lambda sensor 11 is part of an exhaust gas system of an internal combustion engine (not shown). It may be situated upstream or downstream from an exhaust gas catalytic converter in an exhaust pipe of the exhaust gas system in the flow direction, for example. Lambda sensor 11 may also be temporarily removed from the internal combustion engine for the purpose of a diagnosis, however. It is also conceivable that lambda sensor 11 is provided for the initial installation in the internal combustion engine and is connected to diagnostic device 15 for an initial function test. The initial function test may also be carried out when lambda sensor 11 is already installed.

Lambda sensor 11 has a pump cell 17. Pump cell 17 includes an outer pump electrode 19, which is connected to a terminal of plug connector 13 identified by "APE." An inner pump electrode 21 of pump cell 17 is connected to a terminal IPN of plug connector 13. A first solid-state electrolyte 23, which is made of zirconium dioxide, is located between outer pump electrode 19 and inner pump electrode 21. If lambda sensor 11 is installed in the exhaust gas system, a side of pump cell 17 which is delimited by outer pump electrode 19 faces toward an inner chamber of the exhaust pipe of the internal combustion engine, whereas a side of pump cell 17 which is delimited by the inner pump electrode faces toward a diffusion gap (not shown) provided in the interior of lambda sensor 11. Pump cell 17 is therefore located between a side of lambda sensor 11 which faces toward the inner chamber of the exhaust pipe and the diffusion gap of lambda sensor 11.

A measuring cell, which is typically referred to as a Nernst cell 25, is situated between the diffusion gap and a reference air duct (not shown) of lambda sensor 11, which is typically connected to ambient air. Nernst cell 25 has a second solid-state electrolyte 27, on whose side facing toward the diffusion gap a Nernst electrode 29 is situated, which is electrically connected to terminal IPN of plug connector 13. A reference electrode 31 of Nernst cell 25 is situated on a side of second solid-state electrolyte 27 facing toward the reference air duct. Reference electrode 31 is electrically connected to a terminal RE of plug connector 13. In addition, lambda sensor 11 has a heating element 33, which is connected to two terminals H+ and H− of plug connector 13. Heating element 33 and both cells 17 and 25 are integrated into a sensor element of lambda sensor 11, so that heating element 33 is thermally coupled to cells 17, 25, in particular to their solid-state electrolytes 23, 27.

Lambda sensor 11 is constructed according to a suitable manufacturing technology. For example, lambda sensor 11 may be designed as a so-called finger sensor or may be manufactured using a planar technology. Independently of the employed manufacturing technology, lambda sensor 11 has a housing 35, which has an electrically conductive housing part 37, which may be made of metal, for example. Electrically conductive housing part 37 is connected to diagnostic device 15.

Furthermore, a trim resistor 39 is situated in lambda sensor 11, a first terminal of trim resistor 39 being connected to terminal APE of plug connector 13 and a second terminal of trim resistor 39 being connected to terminal RT of plug connector 13. Trim resistor 39 may have a value of approximately 30 ohm to 300 ohm, for example. The value of trim resistor 39 is typically established immediately after the manufacture of the lambda sensor. For this purpose, trim resistor 39 is connected in parallel to a measuring resistor in the regulating electronics. The trim resistor is then set in such a way that a predefined current (e.g., 2.54 mA) results through the measuring resistor when lambda sensor 11 is subjected to a gas having the excess-air ratio λ=1. During operation of lambda sensor 11, manufacturing tolerances of lambda sensor 11 may therefore be at least largely compensated for with the aid of trim resistor 39.

Diagnostic device 15 has a first voltage source 41, which is controllable by a control unit 43 of diagnostic device 15. First voltage source 41 is connected in series to a first current sensor 45. First current sensor 45 is connected to control unit 43, so that control unit 43 may detect a current $I_1$ flowing through first voltage source 41. A terminal of first current sensor 45 which faces away from voltage source 41 is connected to terminal APE of plug connector 13. A side of first voltage source 41 which faces away from first current sensor 45 is connected to a terminal of a first switch element 47 and a second switch element 49. A further terminal of first switch element 47 is connected to terminal RT of plug connector 13. A further terminal of second switch element 49 is connected to terminal IPN of plug connector 13.

A voltage sensor 52 is situated between terminals APE and RE, which is connected to control unit 43 in such a way that it may detect a voltage $U_M$ applied between terminals APE and RE.

Furthermore, diagnostic device 15 has a second voltage source 51, which is connected in series to a second current sensor 53. Second voltage source 51 is controllable and is connected to control unit 43 in such a way that it may set a voltage $U_2$ generated by second voltage source 51 during its operation. Second current sensor 53 is coupled to control unit 43 in such a way that control unit 43 may detect a current $I_2$ flowing through second voltage source 51. A terminal of second current sensor 53 which faces away from second voltage source 51 is connected to terminal IPN of plug connector 13. A terminal of second voltage source 51 which faces away from second current sensor 53 is connected to a third switch element 55 and a fourth switch element 57. A terminal of third switch element 55, which is not directly connected to second voltage source 51, is connected to housing part 37 of lambda sensor 11, and a terminal of fourth switch element 57, which is not directly connected to second voltage source 51, is connected to terminal RE of plug connector 13. Each switch element 47, 49, 55, 57 is coupled to control unit 43, so that control unit 43 may individually activate individual switch elements 47, 49, 55, 57 (corresponding connections are not shown in FIG. 1 for the sake of clarity). As a whole, switch elements 47, 49, 55, 57 form a switch configuration for connecting voltage sources 41, 51 and associated current sensors 45, 53 to individual terminals APE, RT, IPN, RE of plug connector 13 and to the housing. In other specific embodiments of diagnostic device 15, the switch configuration is constructed in another way. The switch elements may be situated on other terminals of plug connector 13, for example, also between a signal electrode and a heater electrode to check the internal leakage current. A different number of switch elements may also be provided. In addition, it is conceivable to provide only one or more than two voltage sources instead of two voltage sources 41, 51 and to increase or decrease the number of the switch elements accordingly. Switch elements 47, 49, 55, 57 may be implemented in any desired way (e.g., semiconductor switches or switch relays).

Furthermore, diagnostic device 15 has a regulating element 59 for regulating a temperature of lambda sensor 11 on the basis of an internal resistance of Nernst cell 25. Regulating element 59 is connected to both terminals H+ and H− of plug connector 13, which are connected to heating element 33 of lambda sensor 11. Regulating element 59 is connected to control unit 43, so that control unit 43 may control regulating element 59 to predefine a setpoint value, for example.

Figure 2:
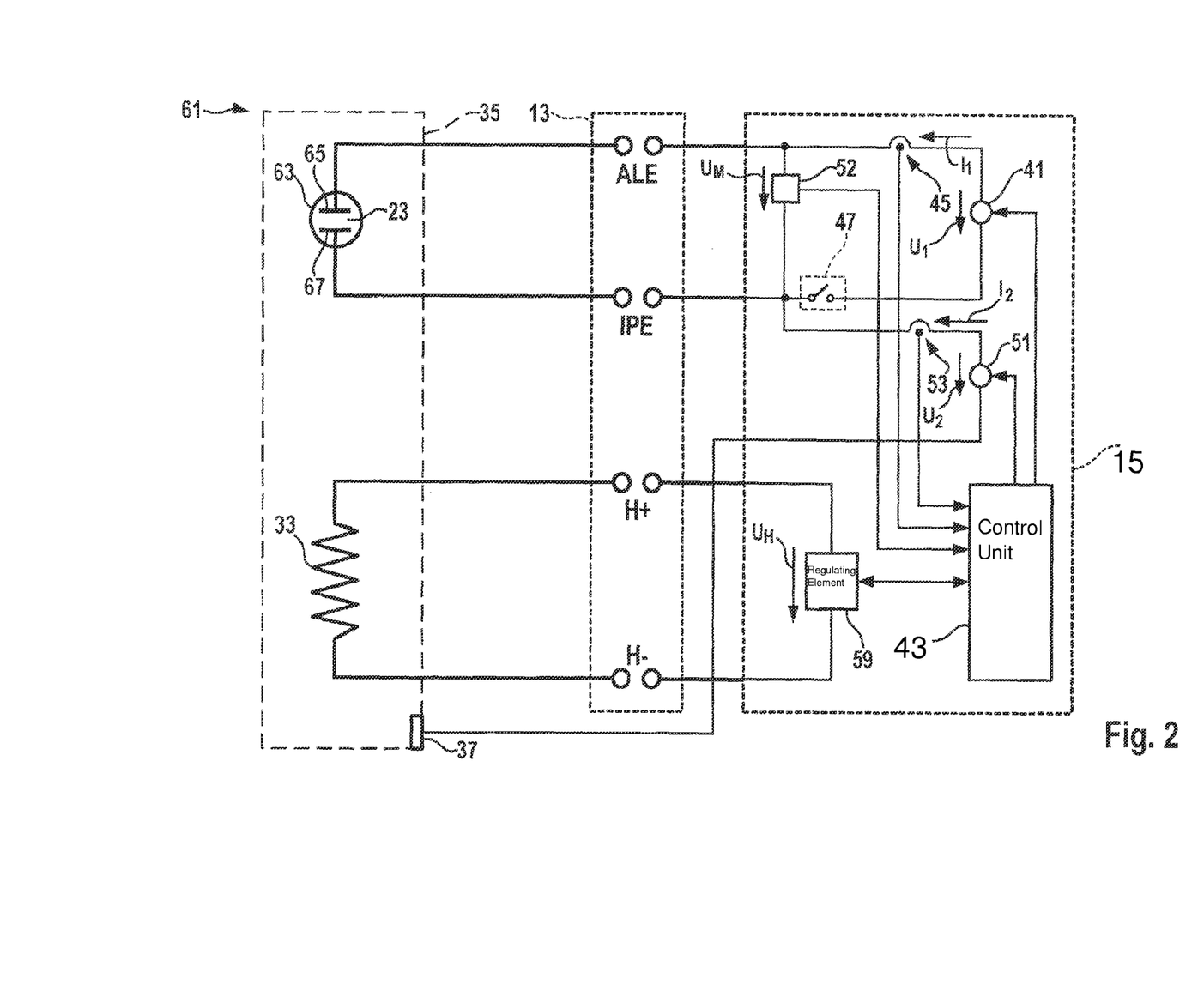
FIG. 2 shows a view similar to FIG. 1, the lambda sensor being a single-chamber broadband lambda sensor.

In the view of FIG. 2, the exhaust gas sensor is designed as a single-cell broadband lambda sensor 61. Instead of pump cell 17 and Nernst cell 25, single-cell broadband lambda sensor 61 has a combined pump and Nernst cell 63. Therefore, only first solid-state electrolyte 23 is provided in this sensor 61. An outer electrode 65 is situated on a side of first solid-state electrolyte 23 which faces toward the inner chamber of the exhaust pipe when sensor 61 is installed. An inner electrode 67 is situated on a side of first solid-state electrolyte 23 which faces away from the inner chamber. Outer electrode 65 is electrically connected to a terminal ALE of plug connector 13, and inner electrode 67 is electrically connected to a terminal IPE of plug connector 13.

Apart from the fact that only one cell 63 is provided in single-cell broadband lambda sensor 61, it has the same design in principle as dual-cell broadband lambda sensor 11 shown in FIG. 1. The respective parts of single-cell broadband lambda sensor 61 are therefore provided with the same reference numerals and will not be explained in detail once again. Simplified diagnostic device 15 shown in FIG. 2 may be connected to single-cell broadband lambda sensor 61. In diagnostic device 15 shown in FIG. 2, third switch element 55 and fourth switch element 57, which are shown in FIG. 1, are not provided. It is also possible to use diagnostic device 15 shown in FIG. 1 in connection with single-cell broadband lambda sensor 61. Terminal RT of diagnostic device 15 may remain free in this case, and combined pump and Nernst cell 63 is connected using its terminal ALE to terminal APE of diagnostic device 15 and using its terminal IPE to terminals IPN and RE of diagnostic device 15.

In a specific embodiment (not shown), single-cell broadband lambda sensor 61 also has trim resistor 39. It may be situated, for example, between terminal ALE and terminal RT, which is not provided in lambda sensor 61 shown in FIG. 2.

A method 71 for diagnosing an exhaust gas sensor, in particular dual-cell lambda sensor 11 or single-cell lambda sensor 61, is explained in greater detail hereafter on the basis of the flow chart shown in FIGS. 3 through 7. This method 71 may be performed using the diagnostic device shown in FIGS. 1 and 2, controlled by its control unit 43. As a deviation, method 71 may also be performed in another way, in particular using differently constructed diagnostic devices and/or other, e.g., dynamic voltage-time programs or current-time programs, which are sinusoidal, for example.

When diagnostic device 15 is used, lambda sensor 11 must be electrically disconnected from the control and/or regulating unit of the internal combustion engine and connected to diagnostic device 15. This may be performed, for example, in that prior to the execution of method 71, plug connector 13 between lambda sensor 11 and the control unit is manually disconnected and a plug connection is manually established between lambda sensor 11 and diagnostic device 15. Method 71 is executed, for example, when the internal combustion engine is shut down or is at a stable operating point. Lambda sensor 11 may remain installed in the internal combustion engine in this case. However, it is also possible to remove lambda sensor 11 from the internal combustion engine prior to executing method 71. Since neither diagnostic device 15 nor lambda sensor 11 is connected to the control unit of the internal combustion engine during the execution of method 71, an isolated diagnosis of lambda sensor 11 may be carried out using method 71. Interactions with the control and/or regulating unit of the internal combustion engine or other parts, in particular sensors and actuators of the internal combustion engine, may be at least largely precluded in this way. This is because the method is executed completely independently of the control and/or regulating unit of the internal combustion engine.

Figure 3:
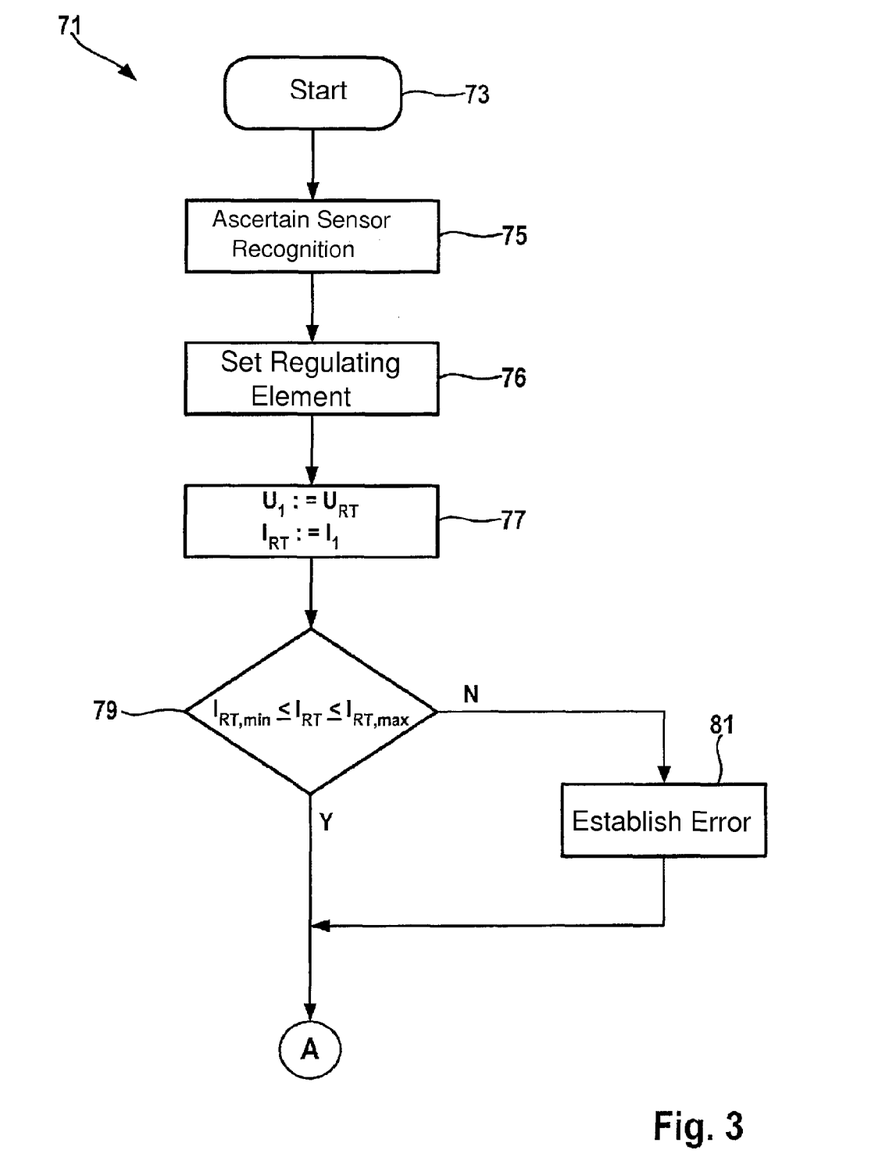
FIG. 3 shows a part of a flow chart as an exemplary embodiment of a method for diagnosing the lambda sensor shown in FIGS. 1 and 2.

After a start 73 of method 71, a type of lambda sensor 11 is ascertained in a sensor recognition step 75. Individual lambda sensors which are used in internal combustion engines for motor vehicles have substantially differing geometries, in particular of individual cells 17, 25, 63, even if they have an identical design in principle (single-cell sensor or dual-cell sensor). Significant differences result therefrom with respect to the electrical properties of lambda sensors 11 of the various types. Sensor recognition step 75 ascertains the type of the sensor by electrical measurements, so that the subsequent steps of method 71 may be executed as a function of the ascertained type of lambda sensor 11.

In a step 76, control unit 43 sets regulating element 59 in such a way that it regulates a temperature of the sensor element of the lambda sensor to a predefined setpoint value. In this case, an internal resistance of Nernst cell 25 or combined pump and Nernst cell 63, which is a function of the temperature of the sensor element, is used as the control variable. A heating power of heating element 33, which regulating element 59 may influence by changing heating voltage $U_H$, for example, is used as the manipulated variable. Control unit 43 ascertains a setpoint value for the internal resistance, which it then predefines to regulating element 59, from the predefined setpoint value of the temperature and a type of the lambda sensor identified in step 75. As a function of the precise embodiment of diagnostic device 15, the setpoint value of the temperature of the sensor element may either be predefined as a constant, or the setpoint value of the temperature may be predefined as a function of the type of the lambda sensor. It may also be provided that control unit 43 ascertains the setpoint value of the internal resistance directly as a function of the type of lambda sensor 11, for example, on the basis of a table stored in control unit 43.

It is subsequently checked in a step 77 whether trim resistor 39 is correctly connected to terminals APE and RT. For this purpose, control unit 43 activates first switch element 47 and second switch element 49 in such a way that only first switch element 47 is closed. Furthermore, the control unit activates first voltage source 41 in such a way that a predetermined voltage $U_{RT}$ is applied to voltage source 41 and therefore also between terminals APE and RT. Subsequently, control unit 43 detects current $I_1$ with the aid of first current sensor 45, which corresponds to a current through trim resistor 39 in the case of intact lambda sensor 11.

Subsequently, it is checked in a branch 79 whether current $I_{RT}$ is within a range delimited by a minimum value $I_{RT,min}$ and a maximum value $I_{RT,max}$. If this is not the case (N), an error is established in a step 81. Control unit 43 may establish and/or log the error in step 81. If the current is less than minimum value $I_{RT,min}$, a bad contact of trim resistor 39 or an interruption between a terminal of trim resistor 39 and one of terminals APE or RT of plug connector 13 is recognized. If detected current $I_{RT}$ is greater than maximum value $I_{RT,max}$, a shunt parallel to trim resistor 39 is recognized. If the detected current is within the permissible range (Y), the sequence branches to a next test step 83. Notwithstanding the specific embodiment shown, the resistance between terminals APE and RT may initially be calculated as a function of predefined voltage $U_{RT}$ and detected current $I_{RT}$ and the calculated resistance may be compared with a permissible resistance range. As a function of this comparison, a bad contact or interruption or a shunt may again be inferred in step 81.

Figure 4:
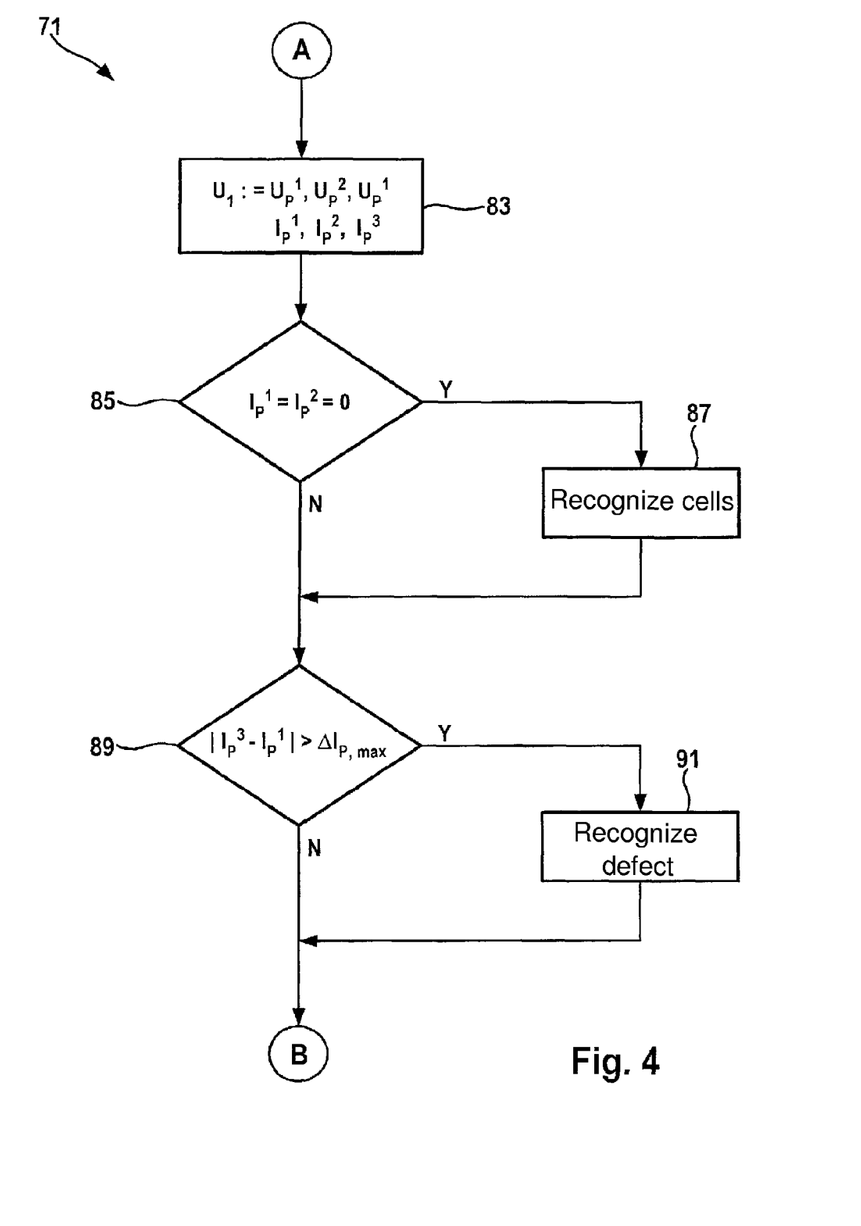
FIG. 4 shows another part of a flow chart as an exemplary embodiment of a method for diagnosing the lambda sensor shown in FIGS. 1 and 2.

Subsequently, a hysteresis within a relationship between a positive pump voltage $U_P > 0$ and a pump current $I_P$ is checked (see FIG. 4). For this purpose, in step 83 a constant voltage $U_1 = U_P > 0$ is applied by voltage source 41 to terminal APE and via closed second switch element 49 to terminal IPN of pump cell 17. In the case of single-cell sensor 61, voltage $U_P$ is applied to terminals ALE and IPE.

The value of pump voltage $U_P$ is varied step-by-step. Initially, no voltage or only a low voltage is applied to pump cell 17 or pump and Nernst cell 63, a relatively small value $U_P^1$, which may be 800 mV, for example, is then applied, and an associated current $I_P^1$ is measured with the aid of first current sensor 45. A higher pump voltage $U_P^2$, which may be 1200 mV, for example, is subsequently applied to terminals APE and IPN or ALE and IPE, and an associated current $I_P^2$ is measured. After a certain time, smaller pump voltage $U_P^1$ is again applied and an associated current $I_P^3$ is detected. Subsequently, a branch 85 checks whether both current values $I_P^1$ and $I_P^2$ are zero. If this is the case (Y), a defect of the lines between terminal APE and/or IPN or ALE and/or IPE and cells 17 or 63 is recognized in a step 87. Otherwise (N), it is checked in a branch 89 whether the absolute value of a difference between currents $I_P^3$ and $I_P^1$ is greater than a maximum value $\Delta I_{P,max}$. If this is the case (Y), a defect on at least one of electrodes 19, 21 or 65, 67 of cells 17 or 63 is recognized in a step 91. If the difference between the currents is less than maximum value $\Delta I_{P,max}$, (branch N of branch 89), the hysteresis is sufficiently small and the sequence branches to a step 93.

In addition, in the case of a dual-cell broadband sensor, during both pump voltages $U_P^1$ and $U_P^2$ having the Ip, the Nernst voltages $U_N^1$ and $U_N^2$ between IPN and RE may also be measured. Both their absolute values and also the difference between them may be used as a diagnostic criterion. The sensitivity to defective IPN is thus improved and, in combination with the results of the Ip hysteresis study, an unambiguous differentiation as to which of the two pump electrodes is defective is made possible.

Figure 5:
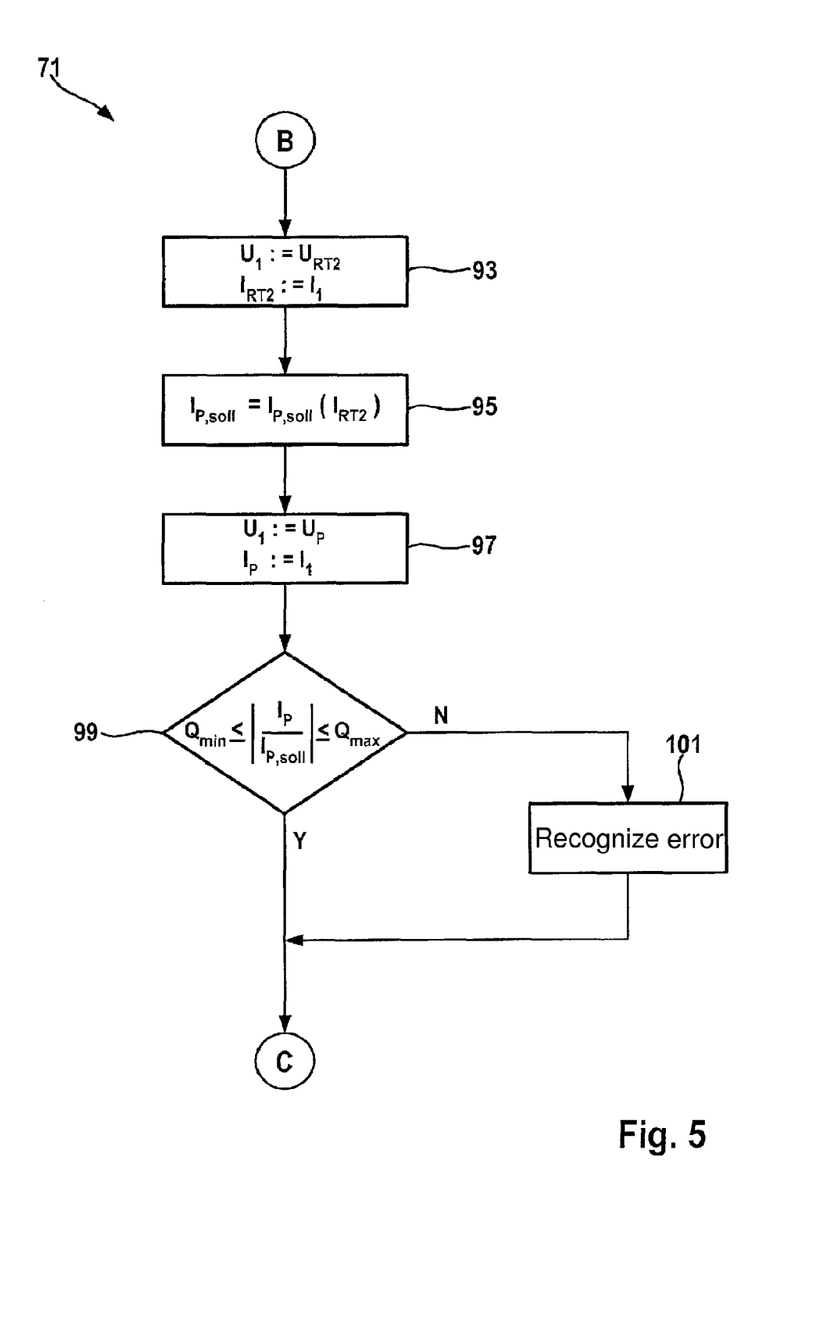
FIG. 5 shows another part of a flow chart as an exemplary embodiment of a method for diagnosing the lambda sensor shown in FIGS. 1 and 2.

In the following steps of method 71, which are shown in FIG. 5, it is checked whether pump current $I_P$ is in a permissible range. For this purpose, in a step 93, a defined constant voltage $U_{RT2}$ is initially applied by appropriate activation of first voltage source 41 and switch elements 47 and 49 and current $I_1$ is detected as a current $I_{RT2}$. A setpoint value $I_{P,setpoint}$ for the pump current is ascertained from detected current $I_{RT2}$ (step 95). Subsequently, a predefined constant positive pump voltage $U_P > 0$ is applied to terminals APE and IPN in a step 97. For this purpose, control unit 43 activates switch elements 47, 49 and first voltage source 41 appropriately ($U_1 = U_P > 0$). Resulting pump current $I_P$ is detected with the aid of first current sensor 45.

Subsequently, it is checked in a branch 99 whether the absolute value of a quotient of detected pump current $I_P$ and ascertained setpoint value $I_{P,setpoint}$ is in a range delimited by values $Q_{min}$ and $Q_{max}$. If this is not the case (N), an error in pump cell 17 is recognized in a step 101. If the quotient is greater than value $Q_{max}$, a crack is recognized in a diffusion barrier of lambda sensor 11 and/or in a sensor ceramic, in particular in first solid-state electrolyte 23. Furthermore, an excessively large value of the quotient indicates an electrical shunt parallel to pump cell 17. If the absolute value of the quotient is less than value $Q_{min}$, sooting, i.e., dirt deposits, on the diffusion barrier is recognized. If the quotient is within the permissible range, the sequence continues with a step 103. The precise value of $Q_{min}$ or $Q_{max}$ may be established as a function of the lambda sensor to be checked and the gas present at the sensor during the diagnosis. For specific types of lambda sensor 11 and specific gas environments, e.g., air, the quotient may deviate upward by up to 14%, i.e., $Q_{max}$=1.14, for example. Correspondingly, a deviation by 14% downward may optionally also be tolerated, i.e., $Q_{min}$=0.86 may be selected, for example.

It is conceivable that steps 93, 95, 97, 99, 101 shown in FIG. 5 for checking the hysteresis are also executed in the case of single-cell sensors and/or sensors without trim resistor 39. In single-cell sensors, pump voltage $U_P$ is applied to terminals ALE and IPE in step 97. In exhaust gas sensors without trim resistor 39, step 93 is omitted, and in step 95, setpoint value $I_{P,setpoint}$ of the pump current is established in another way, for example, as a constant which may optionally be a function of the type of the lambda sensor.

Figure 6:
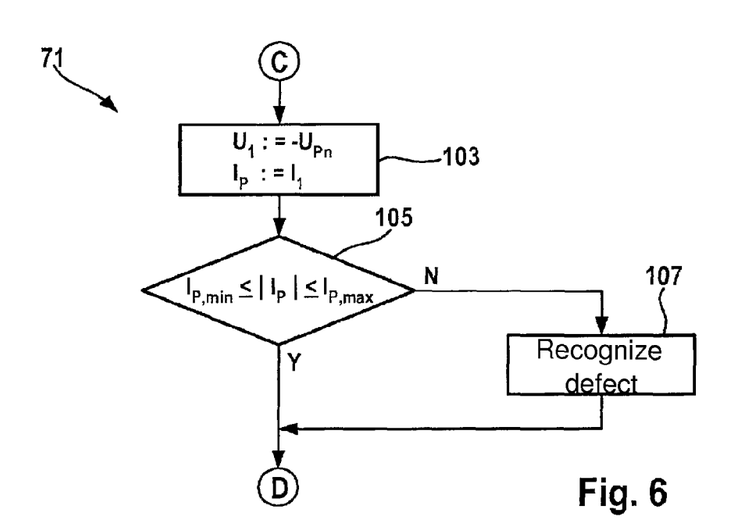
FIG. 6 shows another part of a flow chart as an exemplary embodiment of a method for diagnosing the lambda sensor shown in FIGS. 1 and 2.

Furthermore, in method 71, in addition to pump current $I_P$ in a forward direction, an inverted pump current is also checked. Corresponding steps of method 71 are shown in FIG. 6. In a step 103, a negative voltage $-U_{Pn}$ is generated by first voltage source 41, i.e., $U_1$<0. The negative voltage is applied to terminals APE and IPN or ALE and IPE. For this purpose, control unit 43 closes first switch element 47 and opens second switch element 49. A pump current $I_P$ is detected in the case of applied negative pump voltage $-U_{Pn}$.

A branch 105 following step 103 checks whether the absolute value of detected pump current $I_P$ is within a range delimited by values $I_{P,min}$ and $I_{P,max}$. If this is not the case (N), an error in lambda sensor 11 is established in a step 107. Otherwise (Y), the sequence branches to a step 109. If detected pump current $I_P$ is less than minimum value $I_{P,min}$, sooting of a protective layer applied to outer pump electrode 19 or outer electrode 65, an excessively low temperature of lambda sensor 11, and/or a defect in first solid-state electrolyte 23 are recognized in step 107. If the absolute value of detected pump current $I_P$ is greater than maximum value $I_{P,max}$, an excessively high temperature of lambda sensor 11 and/or an electrical shunt between outer pump electrode 19 and inner pump electrode 21 or outer electrode 65 and inner electrode 67 or damage or a lack of the protective layer are recognized. Such a shunt may originate, for example, due to deposits between electrodes 19 and 21 or 65 and 67 or inadequate insulation of electrodes 19, 21 or 65, 67 from one another.

Figure 7:
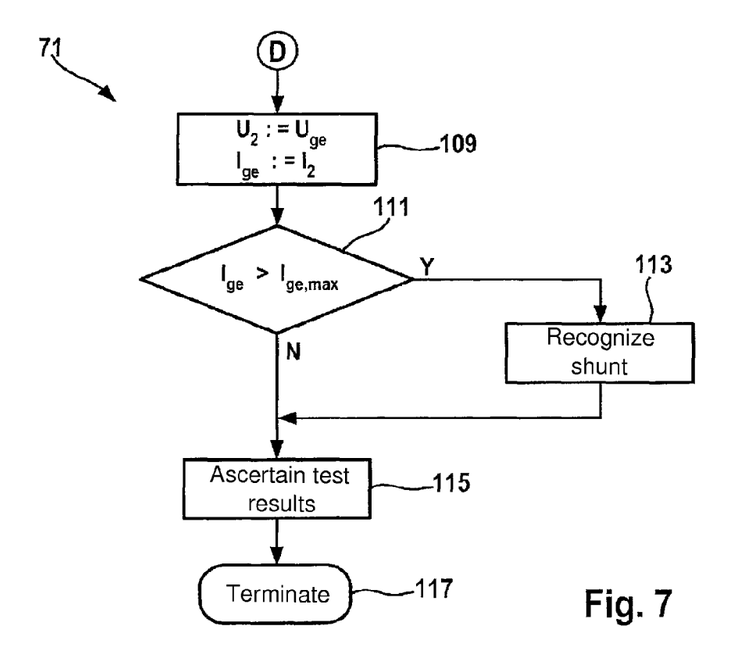
FIG. 7 shows another part of a flow chart as an exemplary embodiment of a method for diagnosing the lambda sensor shown in FIGS. 1 and 2.

As a further check shown in FIG. 7, the electrical conductivity between terminal IPN or IPE and conductive housing part 37 is checked. For this purpose, in step 109, a voltage $U_{ge}$ is applied between terminal IPN or IPE and electrically conductive housing part 37. Voltage $U_{ge}$ may be positive, $U_{ge}$>0. For this purpose, control unit 43 of the diagnostic device shown in FIG. 1 closes third switch element 55 and keeps fourth switch element 57 open. Furthermore, control unit 43 activates second voltage source 51 in such a way that it generates voltage $U_2$=$U_{ge}$. Current $I_2$ flowing through second voltage source 51 is detected as a housing current $I_{ge}$=$I_2$. It is subsequently checked in a branch 111 whether detected housing current $I_{ge}$ is greater than a critical value $I_{ge,krit}$. If this is the case (Y), a shunt is recognized between a sensor element of lambda sensor 11 and housing 35 in a step 113. Such a shunt may originate from sooting of lambda sensor 11, in particular from a soot deposit between the sensor element and an inner side of a protective tube of housing 35. If housing current $I_{ge}$ is not greater than critical value $I_{ge,krit}$ (N), the sequence branches to a step 115. In step 115, the test results ascertained in the preceding steps are analyzed. For example, they may be displayed and/or stored. It is also conceivable that, in particular if all tests have not delivered error findings individually, a multidimensional feature spectrum is checked. This means that the tolerance ranges of each individual studied functional variable are linked in a final test to where each of the other functional values lie. A more sensitive overall diagnosis may thus be achieved and interactions between individual parameters may also be considered. Subsequently, the method is terminated in step 117.

In the shown specific embodiment of method 71, for the case in which an individual check recognizes an error, i.e., for the case in which one of steps 81, 87, 91, 101, 107, or 113 is executed, method 71 is continued in each case using the next check. This means that all checks are performed independently of the results of the particular preceding check. In this case, control unit 43 controls the sequence of method 71 and analyzes detected variables for the diagnosis of lambda sensor 11, 61. Control unit 43 therefore also forms an analysis unit of diagnostic device 15.

However, as a deviation it may also be provided that method 71 is terminated as soon as one of the checks recognizes an error. In this case, after execution of steps 81, 87, 91, 101, or 107, the sequence immediately branches to step 115. The sequence of the particular checks shown in FIGS. 3 through 7 may be varied arbitrarily. In other specific embodiments, these checks may also be individually omitted.

Figure 8:
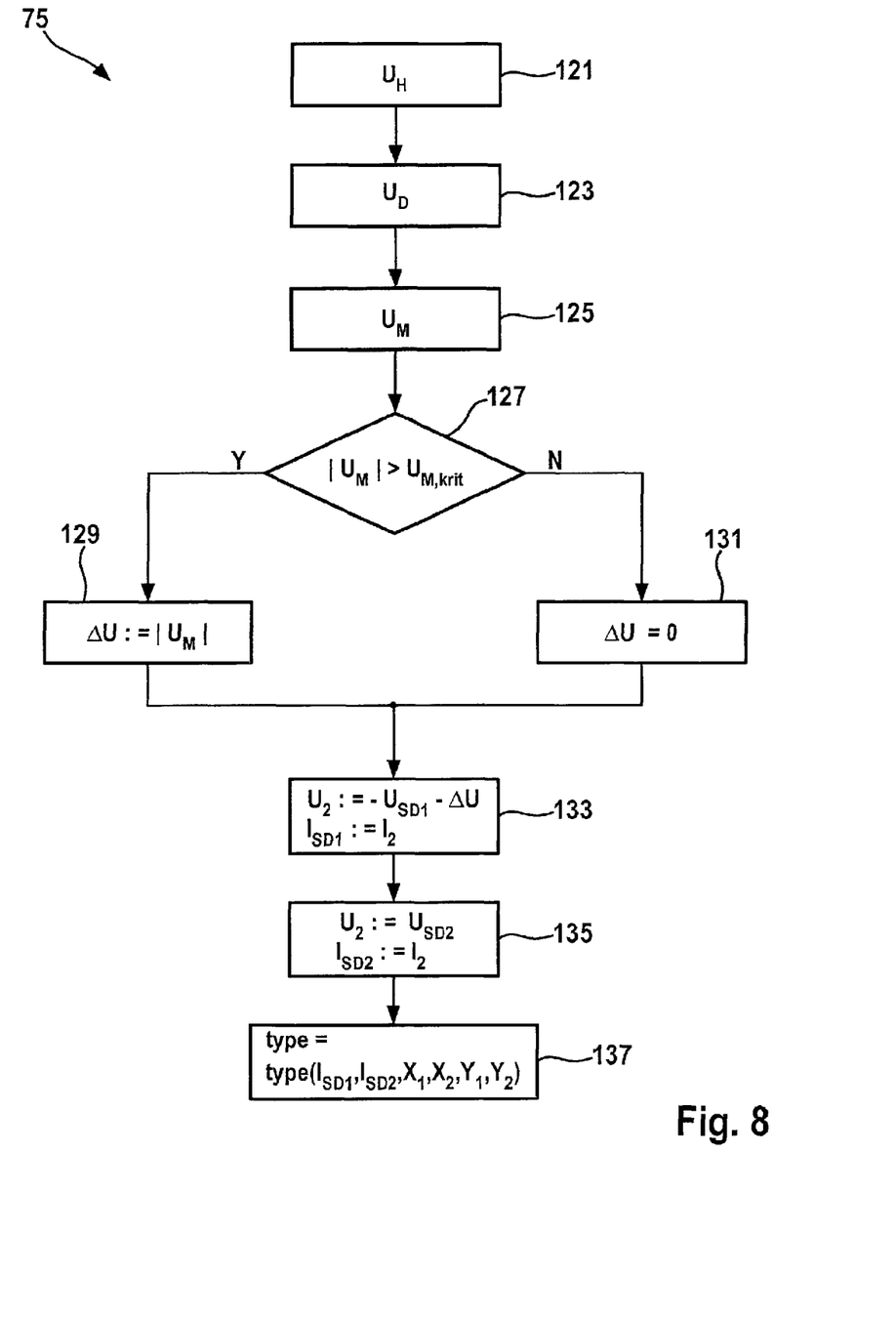
FIG. 8 shows a more detailed view of a step of the method from FIGS. 3 through 7.

Step 75 for recognizing the type of lambda sensor 11 is explained in greater detail hereafter on the basis of FIG. 8. In step 75, control unit 43 initially activates regulating element 59 in such a way that a heating voltage $U_H$ is applied between terminal H+ and terminal H− of lambda sensor 11 (step 121). An exact regulation of the temperature of lambda sensor 11 is not necessary for recognizing the type of lambda sensor 11. Heating voltage $U_H$ must only be sufficiently high so that for all sensor types, with which diagnostic device 15 is to be operated, a sufficiently high temperature of solid-state electrolytes 23, 27 is achieved at which solid-state electrolytes 23, 27 are able to conduct oxygen ions. In a subsequent step 123, oxygen ions are transported to the diffusion gap of lambda sensor 11. If lambda sensor 11 is a dual-cell sensor, a negative voltage $U_D$<0 is applied to Nernst cell 25. For this purpose, control unit 43 activates second voltage source 51 in such a way that voltage $U_2$ has a negative value, i.e., $U_2$=$U_D$<0. After a certain time, Nernst cell 25 is again disconnected from voltage $U_D$. For this purpose, control unit 43 may open fourth switch element 57.

In a step 125 following step 123, a voltage $U_M$ between terminal APE and terminal RE, i.e., essentially a voltage between outer pump electrode 19 and reference electrode 31, is detected with the aid of voltage sensor 52. The level of voltage $U_M$ is a measure for the oxygen content in the gas which is present on the side of lambda sensor 11 which faces toward outer pump electrode 19. If this is oxygen-poor gas, a relatively high value results for voltage $U_M$, which is typically greater than 450 mV. Steps 123 and 125 are therefore used to recognize oxygen-poor gas (rich gas recognition). Oxygen-poor gas may be present in particular if lambda sensor 11 remains installed in the exhaust pipe of the internal combustion engine during the diagnosis. This is because residual exhaust gas often remains in the exhaust pipe, which has a relatively low oxygen content, after a shutdown of the internal combustion engine for the purpose of diagnosis. Since the exhaust system, in particular the exhaust pipe in which lambda sensor 11 is installed, is sealed relatively well in relation to the ambient air in modern internal combustion engines, the oxygen content in the exhaust pipe only rises slightly at most, even after a longer shutdown of the internal combustion engine.

If lambda sensor 11 is single-cell sensor 61, voltage $U_D$ is applied to terminals ALE and IPE in step 123. For this purpose, control unit 43 activates first voltage source 41 in such a way that it generates positive voltage $U_D>0$, i.e., $U_1=U_D>0$. In step 125, voltage $U_M$ between terminals ALE and IPE is measured with the aid of voltage sensor 52.

Subsequently, it is checked in a branch 127 whether the absolute value of detected voltage $U_M$ is greater than a critical value $U_{M,krit}$. If this is the case (Y), it is recognized that oxygen-poor, i.e., rich, gas is present, and a correction value $\Delta U$ is set to a value which corresponds to the absolute value of voltage $U_M$ in a step 129. Otherwise (N), correction value $\Delta U$ is set to zero in a step 131.

Step 129 or 131 is followed by a step 133, in which a negative voltage is applied between terminal IPN and terminal RE. The absolute value of this voltage corresponds to a predetermined value $U_{SD1}>0$, which is corrected by correction value $\Delta U>0$, i.e., second voltage source 51 generates voltage $U_2=-U_{SD1}-\Delta U<0$. Current $I_2$ is simultaneously detected as pump current $I_{SD2}$. Subsequently, a positive predefined constant voltage $U_{SD2}>0$ is applied to terminals IPN and RE in a step 135, whereby the polarity of the voltage at terminals IPN and RE is reversed. Current $I_2$ is simultaneously detected as further pump current $I_{SD2}$. Finally, in a step 137, the type of lambda sensor 11 is ascertained as a function of both detected pump currents $I_{SD1}$ and $I_{SD2}$. After completing step 137, method 71 continues with step 76, which follows step 75.

For example, two types of lambda sensor 11 may be differentiated on the basis of detected pump currents $I_{SD1}$ and $I_{SD2}$ which differ with respect to their geometry, in particular the size of the air diffusion duct to reference electrode 31 or the size and location of Nernst electrode 29.

Due to the different geometries, a resistance of Nernst cell 25 of lambda sensor 11 of these different types is therefore different. A relatively great value for detected currents $I_{SD1}$ and $I_{SD2}$ therefore results in lambda sensor 11 of the type in which Nernst cell 25 has a small ohmic resistance and an open reference air duct. In lambda sensor 11 of the type in which the ohmic resistance of Nernst cell 25 is relatively large and the diffusion coefficient of the reference air duct is relatively small, these detected currents $I_{SD1}$ and $I_{SD2}$ are relatively small. It may thus be provided that in step 137, the type of lambda sensor 11, in which the resistance of Nernst cell 25 and the reference air duct is small, is recognized if the detected currents are both greater than specific predefined minimum values, i.e., if $I_{SD1}>X_1$ and $I_{SD2}>X_2$. Correspondingly, it may be provided in step 137 that the type of lambda sensor 11, in which the resistance of Nernst cell 25 and of the reference air duct is high, is recognized if the detected currents are less than specific predefined minimum values, i.e., if $I_{SD1}<Y_1$ and $I_{SD2}<Y_2$. Other, contrary combinations between the detected currents may also characterize a sensor type.

Above-described steps 133, 135, 137 for differentiating types of lambda sensor 11 may also be applied accordingly in connection with single-cell lambda sensor 61.

It is recognized that the above-described check is redundant in that two detected currents are checked in order to differentiate between two different types of the lambda sensor. This allows a particularly reliable differentiation of the types of lambda sensor 11. In the cases in which the type of lambda sensor 11 cannot be unambiguously identified, method 71 may either be aborted or a user of diagnostic device 15 may be requested to manually input the type of lambda sensor 11. In step 137, it is established that the type of lambda sensor 11 cannot be unambiguously identified if neither of the two above-mentioned conditions with respect to currents $I_{SD1}$ and $I_{SD2}$ apply. In this way, incorrect identification of the type of lambda sensor 11 is avoided, for example, if the resistance of Nernst cell 25 has changed due to wear or aging effects (so-called dynamic effects) of lambda sensor 11.

Overall, the exemplary embodiments and/or exemplary methods of the present invention provide a method and a diagnostic device, using which a detail check of an exhaust gas sensor, in particular a lambda sensor, is possible, the check being able to be performed isolated from other components of the internal combustion engine, which may be when the internal combustion engine is shut down. In this way, effects corrupting the check as a result of interactions between various components of the internal combustion engine are at least largely eliminated. Easy operation of diagnostic device 15 is achieved by the automatic recognition of the type of lambda sensor 11.

What is claimed is:

1. A method for diagnosing an electrochemical sensor, which is a heatable exhaust gas sensor of an internal combustion engine, the method comprising:
   performing one of the following sets (a) and (b) of operations:
   (a) generating a predefined chronologically varying or constant voltage with the aid of a voltage source;
       applying the voltage to terminals/electrodes of the exhaust gas sensor;
       detecting a current, which flows through the voltage source when the voltage is applied, is detected; and
       analyzing the current to diagnose the exhaust gas sensor; and
   (b) generating a predefined chronologically varying or constant current with the aid of a voltage source;
       driving the current through the terminals/electrodes of the exhaust gas sensor;
       applying a voltage, which is applied to the voltage source when the current is fed;
       detecting the voltage, which is applied to the voltage source when the current is fed; and
       analyzing a voltage to diagnose the exhaust gas sensor;
   wherein the method is executed independently of a control and/or regulating unit of the internal combustion engine, and wherein an operating temperature of the exhaust gas sensor is regulated to a predefined temperature value with the aid of a regulating element, which is separate from the control and/or regulating unit, and
   wherein the voltage is applied to the terminals, which are connected to electrode of a cell of the exhaust gas sensor, and a pump current is detected as the current.

2. The method of claim 1, wherein the voltage is varied step-by-step and/or in alternating directions in such a way that the voltage successively has different voltage values, and associated current values of the current are detected for at least two of these voltage values.

3. The method of claim 2, wherein a hysteresis with respect to a dependence between the applied voltage and the detected current is checked by analyzing the current values by comparing the current values with one another.

4. The method of claim 2, wherein a hysteresis with respect to a dependence between the applied voltage and a detected Nernst voltage is checked by analyzing Nernst voltage values between RE and IPN by comparing the Nernst voltage values with one another.

5. A method for diagnosing an electrochemical sensor, which is a heatable exhaust gas sensor of an internal combustion engine, the method comprising:
  performing one of the following sets (a) and (b) of operations:
  (a) generating a predefined chronologically varying or constant voltage with the aid of a voltage source;
    applying the voltage to terminals/electrodes of the exhaust gas sensor;
    detecting a current, which flows through the voltage source when the voltage is applied, is detected; and
    analyzing the current to diagnose the exhaust gas sensor; and
  (b) generating a predefined chronologically varying or constant current with the aid of a voltage source;
    driving the current through the terminals/electrodes of the exhaust gas sensor;
    applying a voltage, which is applied to the voltage source when the current is fed;
    detecting the voltage, which is applied to the voltage source when the current is fed; and
    analyzing a voltage to diagnose the exhaust gas sensor;
  wherein the method is executed independently of a control and/or regulating unit of the internal combustion engine, and wherein an operating temperature of the exhaust gas sensor is regulated to a predefined temperature value with the aid of a regulating element, which is separate from the control and/or regulating unit, and
  wherein the voltage is applied to the terminals which are connected to a trim resistor of the exhaust gas sensor.

6. The method of claim 5, wherein, as a function of a value of the trim resistor, a setpoint value for a pump current is ascertained, wherein a positive pump voltage is applied as the voltage, and wherein the exhaust gas sensor is checked as a function of the setpoint value and the pump current.

7. The method of claim 6, wherein a negative pump voltage is applied as the voltage, wherein an inverted pump current is detected as the current, and wherein it is checked whether the inverted pump current is in a predefined permissible range.

8. A method for diagnosing an electrochemical sensor, which is a heatable exhaust gas sensor of an internal combustion engine, the method comprising:
  performing one of the following sets (a) and (b) of operations:
  (a) generating a predefined chronologically varying or constant voltage with the aid of a voltage source;
    applying the voltage to terminals/electrodes of the exhaust gas sensor;
    detecting a current, which flows through the voltage source when the voltage is applied, is detected; and
    analyzing the current to diagnose the exhaust gas sensor; and
  (b) generating a predefined chronologically varying or constant current with the aid of a voltage source;
    driving the current through the terminals/electrodes of the exhaust gas sensor;
    applying a voltage, which is applied to the voltage source when the current is fed;
    detecting the voltage, which is applied to the voltage source when the current is fed; and
    analyzing a voltage to diagnose the exhaust gas sensor;
  wherein the method is executed independently of a control and/or regulating unit of the internal combustion engine, and wherein an operating temperature of the exhaust gas sensor is regulated to a predefined temperature value with the aid of a regulating element, which is separate from the control and/or regulating unit, and
  wherein the voltage is applied between a terminal of the exhaust gas sensor, which is connected to an electrode of the cell, which is an inner electrode of a pump cell, and an electrically conductive housing part of the exhaust gas sensor, a housing current is detected as the current, and it is checked whether the housing current is less than or equal to a predefined maximum value.

9. A method for diagnosing an electrochemical sensor, which is a heatable exhaust gas sensor of an internal combustion engine, the method comprising:
  performing one of the following sets (a) and (b) of operations:
  (a) generating a predefined chronologically varying or constant voltage with the aid of a voltage source;
    applying the voltage to terminals/electrodes of the exhaust gas sensor;
    detecting a current, which flows through the voltage source when the voltage is applied, is detected; and
    analyzing the current to diagnose the exhaust gas sensor; and
  (b) generating a predefined chronologically varying or constant current with the aid of a voltage source;
    driving the current through the terminals/electrodes of the exhaust gas sensor;
    applying a voltage, which is applied to the voltage source when the current is fed;
    detecting the voltage, which is applied to the voltage source when the current is fed; and
    analyzing a voltage to diagnose the exhaust gas sensor;
  wherein the method is executed independently of a control and/or regulating unit of the internal combustion engine, and wherein an operating temperature of the exhaust gas sensor is regulated to a predefined temperature value with the aid of a regulating element, which is separate from the control and/or regulating unit, and
  wherein at least one measured variable, which characterizes a cell resistance of the at least one cell of the exhaust gas sensor, which is the cell resistance of a Nernst cell of the exhaust gas sensor, is detected or ascertained, and a type of the exhaust gas sensor is ascertained as a function of the measured variable.

10. The method of claim 9, wherein at least one measuring voltage is applied to the cell as the voltage, and the current through the cell is detected as the measured variable for each measured voltage.

11. The method of claim 10, wherein at least two measuring voltages of different polarity are applied to the cell in succession.

12. The method of claim 9, wherein each measured variable is compared with a threshold value, and the type of the exhaust gas sensor is ascertained as a function of this comparison.

13. The method of claim 10, wherein, prior to the application of the measuring voltage to the cell, a cell voltage generated by the cell is detected, and at least one of the mentioned measured voltages is predefined as a function of the cell voltage.

14. A diagnostic device for checking a heatable exhaust gas sensor of an internal combustion engine, comprising:
- one of the following sets (a) and (b) of components:
  - (a) at least one voltage source, which is configured to apply a predefined chronologically varying or constant voltage to terminals of the exhaust gas sensor;
  - at least one current sensor, which is configured to detect a current which flows through the voltage source when the voltage is applied; and
  - an analysis unit for analyzing the current to diagnose the exhaust gas sensor; and
  - (b) at least one voltage source, which is configured to generate a predefined chronologically varying or constant current, and which is configured for driving the current through terminals of the exhaust gas sensor;
  - a voltage sensor, which is configured to detect a voltage applied to the voltage source when the current is fed; and
  - an analysis unit, which is configured to analyze the voltage for diagnosing an electrochemical sensor;
- wherein the diagnostic device is separated from a control and/or regulating unit of the internal combustion engine so that it may check the exhaust gas sensor independently of a control and/or regulating unit, the diagnostic device having a regulating element for regulating an operating temperature of the exhaust gas sensor to a predefined value, and
- wherein the voltage is applied to the terminals, which are connected to electrode of a cell of the exhaust gas sensor, and a pump current is detected as the current.

15. The diagnostic device of claim 14, wherein the voltage is varied step-by-step and/or in alternating directions so that the voltage successively has different voltage values, and associated current values of the current are detected for at least two of these voltage values.

16. The diagnostic device of claim 15, wherein a hysteresis with respect to a dependence between the applied voltage and the detected current is checked by analyzing the current values by comparing the current values with one another.

17. The diagnostic device of claim 15, wherein a hysteresis with respect to a dependence between the applied voltage and a detected Nernst voltage is checked by analyzing Nernst voltage values between RE and IPN by comparing the Nernst voltage values with one another.

18. A diagnostic device for checking a heatable exhaust gas sensor of an internal combustion engine, comprising:
- one of the following sets (a) and (b) of components:
  - (a) at least one voltage source, which is configured to apply a predefined chronologically varying or constant voltage to terminals of the exhaust gas sensor;
  - at least one current sensor, which is configured to detect a current which flows through the voltage source when the voltage is applied; and
  - an analysis unit for analyzing the current to diagnose the exhaust gas sensor; and
  - (b) at least one voltage source, which is configured to generate a predefined chronologically varying or constant current, and which is configured for driving the current through terminals of the exhaust gas sensor;
  - a voltage sensor, which is configured to detect a voltage applied to the voltage source when the current is fed; and
  - an analysis unit, which is configured to analyze the voltage for diagnosing an electrochemical sensor;
- wherein the diagnostic device is separated from a control and/or regulating unit of the internal combustion engine so that it may check the exhaust gas sensor independently of a control and/or regulating unit, the diagnostic device having a regulating element for regulating an operating temperature of the exhaust gas sensor to a predefined value, and
- wherein the voltage is applied to the terminals which are connected to a trim resistor of the exhaust gas sensor.

19. The diagnostic device of claim 18, wherein, as a function of a value of the trim resistor, a setpoint value for a pump current is ascertained, wherein a positive pump voltage is applied as the voltage, and wherein the exhaust gas sensor is checked as a function of the setpoint value and the pump current.

20. The diagnostic device of claim 19, wherein a negative pump voltage is applied as the voltage, wherein an inverted pump current is detected as the current, and wherein it is checked whether the inverted pump current is in a predefined permissible range.

21. A diagnostic device for checking a heatable exhaust gas sensor of an internal combustion engine, comprising:
- one of the following sets (a) and (b) of components:
  - (a) at least one voltage source, which is configured to apply a predefined chronologically varying or constant voltage to terminals of the exhaust gas sensor;
  - at least one current sensor, which is configured to detect a current which flows through the voltage source when the voltage is applied; and
  - an analysis unit for analyzing the current to diagnose the exhaust gas sensor; and
  - (b) at least one voltage source, which is configured to generate a predefined chronologically varying or constant current, and which is configured for driving the current through terminals of the exhaust gas sensor;
  - a voltage sensor, which is configured to detect a voltage applied to the voltage source when the current is fed; and
  - an analysis unit, which is configured to analyze the voltage for diagnosing an electrochemical sensor;
- wherein the diagnostic device is separated from a control and/or regulating unit of the internal combustion engine so that it may check the exhaust gas sensor independently of a control and/or regulating unit, the diagnostic device having a regulating element for regulating an operating temperature of the exhaust gas sensor to a predefined value, and
- wherein the voltage is applied between a terminal of the exhaust gas sensor, which is connected to an electrode of the cell, which is an inner electrode of a pump cell, and an electrically conductive housing part of the exhaust gas sensor, a housing current is detected as the current, and it is checked whether the housing current is less than or equal to a predefined maximum value.

22. A diagnostic device for checking a heatable exhaust gas sensor of an internal combustion engine, comprising:
- one of the following sets (a) and (b) of components:
  - (a) at least one voltage source, which is configured to apply a predefined chronologically varying or constant voltage to terminals of the exhaust gas sensor;
  - at least one current sensor, which is configured to detect a current which flows through the voltage source when the voltage is applied; and
  - an analysis unit for analyzing the current to diagnose the exhaust gas sensor; and
  - (b) at least one voltage source, which is configured to generate a predefined chronologically varying or constant current, and which is configured for driving the current through terminals of the exhaust gas sensor;
  - a voltage sensor, which is configured to detect a voltage applied to the voltage source when the current is fed; and an analysis unit, which is configured to analyze the voltage for diagnosing an electrochemical sensor;

wherein the diagnostic device is separated from a control and/or regulating unit of the internal combustion engine so that it may check the exhaust gas sensor independently of a control and/or regulating unit, the diagnostic device having a regulating element for regulating an operating temperature of the exhaust gas sensor to a predefined value, and wherein at least one measured variable, which characterizes a cell resistance of the at least one cell of the exhaust gas sensor, which is the cell resistance of a Nernst cell of the exhaust gas sensor, is detected or ascertained, and a type of the exhaust gas sensor is ascertained as a function of the measured variable.

23. The diagnostic device of claim 22, wherein at least one measuring voltage is applied to the cell as the voltage, and the current through the cell is detected as the measured variable for each measured voltage.

24. The diagnostic device of claim 23, wherein at least two measuring voltages of different polarity are applied to the cell in succession.

25. The diagnostic device of claim 22, wherein each measured variable is compared with a threshold value, and the type of the exhaust gas sensor is ascertained as a function of this comparison.

26. The diagnostic device of claim 23, wherein, prior to the application of the measuring voltage to the cell, a cell voltage generated by the cell is detected, and at least one of the mentioned measured voltages is predefined as a function of the cell voltage.

\* \* \* \* \*